United States Patent [19]
Peyman

[11] Patent Number: 6,033,395
[45] Date of Patent: Mar. 7, 2000

[54] SYSTEM AND METHOD FOR MODIFYING A LIVE CORNEA VIA LASER ABLATION AND MECHANICAL EROSION

[76] Inventor: Gholam A. Peyman, 8654 Pontchartrain Blvd., Unit 1, New Orleans, La. 70124

[21] Appl. No.: 08/962,716

[22] Filed: Nov. 3, 1997

[51] Int. Cl.[7] .................................................. A61B 17/36
[52] U.S. Cl. .................................................. 606/4; 606/13
[58] Field of Search ........................ 604/19, 22; 606/161, 606/166, 4–5, 160, 162

[56] References Cited

U.S. PATENT DOCUMENTS

| | | |
|---|---|---|
| 3,818,913 | 6/1974 | Wallach . |
| 4,634,420 | 1/1987 | Spinosa et al. ............................ 604/22 |
| 4,744,360 | 5/1988 | Bath . |
| 4,770,172 | 9/1988 | L'Esperance, Jr. . |
| 4,840,175 | 6/1989 | Peyman . |
| 5,112,328 | 5/1992 | Taboada et al. ............................ 606/4 |
| 5,215,104 | 6/1993 | Steinert . |
| 5,246,436 | 9/1993 | Rowe ............................ 606/13 |
| 5,591,185 | 1/1997 | Kilmer et al. ............................ 606/166 |
| 5,649,943 | 7/1997 | Amoils ............................ 606/161 |
| 5,792,160 | 8/1998 | Weiss et al. ............................ 606/161 |

OTHER PUBLICATIONS

Gholam A. Peyman & Naoko Katoh, "Effects of an erbium:YAG laser on ocular structures", *International Ophthalmology*, vol. 10, 1987, pp. 245–253.

Peyman et al, "Long–term effect of erbium–YAG laser (2.9 $\mu$m) on the primate cornea", *International Ophthalmology*, vol. 15, 1991, pp. 249–258.

Peyman et al, "Corneal Ablation in Rabbits Using an Infrared (2.9 $\mu$m) Erbium–YAG Laser", *Ophthalmology*, vol. 96, No. 8, Aug. 1989, pp. 1160–1170.

Seiler et al, "Erbium:YAG Laser Photoblation of Human Cornea", *American Journal of Ophthalmology*, vol. 120, No. 5, Nov. 1995, pp. 668–669.

José I. Barraquer, M.D., "Keratomileusis for Myopia and Aphakia", *Ophthalmology*, vol. 88, Aug. 1981, pp. 701–708.

José I. Barraquer, M.D., "Keratomileusis and Keratophakia in the Surgical Correction of Aphakia", *Cataract Surgery and Special Techniques*, Chapter 7, (published prior to 1996), pp. 270–289.

"Keratotomy, Keratectomy, Keratocryotherapy, Keratabrasion, Thermokeratoplasty, and Keratotattooing", *Advanced Techniques in Ophthalmic Microsurgery*, Chapter 4, (published prior to 1997), pp. 107–141.

*Primary Examiner*—Linda C. M. Dvorak
*Assistant Examiner*—Roy Gibson
*Attorney, Agent, or Firm*—Roylance, Abrams, Berdo & Goodman, L.L.P.

[57] ABSTRACT

A system and method for using an infrared laser and, in particular, an Er:YAG laser to modify an interior or exterior surface of a live cornea, and then a tool to physically remove (e.g., erode) a coagulated portion of the cornea that is created due to irradiation of the cornea by the laser light. The tool includes a tip made of any suitable type of material that can be used to physically remove all or substantially all of the coagulated portion of the cornea, while not removing any or essentially any of the underlying corneal tissue. An irrigation/aspiration system can be used in conjunction with the tool to facilitate removal of the coagulated portion of the cornea. Furthermore, a fluid delivery system can be used to deliver a fluid which physically removes the coagulated portion of the cornea. These tools and fluid delivery systems can alternately be used to remove substantially all of the coagulated corneal tissue, and then another tool, such as, a fluid delivery system type tool or a tool having a tip made of a different material, can be used to remove the remaining portion of the coagulated area and polish the underlying remaining corneal tissue exposed after the coagulated area has been removed.

17 Claims, 7 Drawing Sheets

SYSTEM AND METHOD FOR MODIFYING A LIVE CORNEA VIA LASER ABLATION AND MECHANICAL EROSION

BACKGROUND OF THE INVENTION

1. Field of the Invention

The present invention relates to a system and method for modifying a live cornea by ablating an exterior or interior surface of the live cornea with laser radiation, and then eroding the irradiated surface with a mechanical eroding tool to remove a coagulated portion of the cornea created by the laser ablation. More specifically, the present invention relates to a system and method which uses an infrared, and preferably an erbium:YAG, laser to ablate a portion of an exterior or interior surface of a live cornea, and then a mechanical eroding tool which includes a material that is placed in contact with the irradiated surface of the cornea to physically remove (e.g., erode) a coagulated portion of the cornea created by the laser ablation, to alleviate cloudiness in the modified live cornea and reduce the healing time.

2. Description of the Related Art

Various surgical techniques presently exist for correcting ametropic conditions of the eye, such as myopia, hypermetropia or hyperopia, and astigmatism. In a normal emetropic eye, which includes a cornea, lens and retina, the cornea and lens cooperatively focus light entering the eye from a far point (i.e., infinity) onto the retina. However, in an ametropic eye, the cornea and lens are incapable of correctly focusing the far point on the retina.

For instance, in a myopic eye, the cornea or lens has a refractive power stronger than that of the cornea and lens of an emetropic eye, or the axial length of the myopic eye is longer than that of a normal emetropic eye. The stronger refractive power or longer axial length causes the far point to be projected in front of the retina.

Conversely, a hypermetropic or hyperopic eye has an axial length shorter than that of a normal emetropic eye, or a lens or cornea having a refractive power less than that of a lens and cornea of an emetropic eye. This lesser refractive power or shorter axial length causes the far point to be focused in back of the retina.

An eye suffering from astigmatism, on the other hand, has a defect in the lens or shape of the cornea. Therefore, an astigmatic eye is incapable of sharply focusing images on the retina.

Perhaps the most common technique for correcting the vision in an eye suffering from ametropic conditions is the use of glasses. In this technique, a lens is placed in front of the eye (i.e., in the form of glasses or a contact lens) to compensate for the focusing defect in the cornea and lens of the eye. However, glasses and contact lenses are often lost and have to be replaced.

Surgical techniques have also been developed to correct these more severe forms of ametropia. Many of these surgical techniques involve the modification or reshaping of the surface of the cornea, which changes the refractive power of the cornea and thus corrects the focusing defect in the eye. The shape of the cornea can be modified by surgically cutting the cornea with a microkeratome, for example, or by inserting an organic or synthetic artificial lens inside the cornea.

A further surgical technique employs the use of ultraviolet and shorter wavelength lasers which are commonly known as excimer lasers that produce pulsed ultraviolet radiation. In one type of laser surgical technique, the pulsed ultraviolet radiation is directed onto the outer surface of the cornea to ablate portions of the cornea and thus modify or reshape the surface of the cornea. However, this technique (photorefractive keratectomy) is generally ineffective in correcting high myopia of 6 diopters or greater, and is also ineffective in correcting severe astigmatisms and severe forms of hypermetropia or hyperopia.

Another surgical technique known as laser in situ keratomycosis (LASIK) has been previously developed by the present inventor as disclosed in U.S. Pat. No. 4,840,175 to Peyman, the entire contents of which is incorporated herein by reference. In this technique, a portion of the front of the live cornea can be cut away in the form of a flap having a thickness of about 160 microns. This cut portion is removed from the live cornea to expose an inner surface of the cornea. A laser beam generated by an excimer laser is directed onto the exposed inner surface to ablate a desired amount of the surface up to about 150–180 microns deep. A cut portion is than reattached over the ablated portion of the cornea, and assumes the shape conforming to that of the ablated portion.

Although the above-mentioned laser surgery techniques are very effective in modifying the shape of the cornea and thus correcting the ametropic conditions discussed above, several problems with excimer lasers exist. For instance, an excimer laser is very expensive. Typical excimer lasers, such as the argon-fluoride, krypton-fluoride and xenon-chloride lasers, can cost between $400,000 and $500,000. Furthermore, these types of excimer lasers usually include halogen gases such as fluorine and chlorine, which are highly toxic and require special handling. Specifically, if the chlorine or fluorine gas needs to be replaced, a skilled technical often needs to perform the servicing.

In an attempt to alleviate these problems associated with excimer lasers, the present inventor has experimented with infrared lasers, such as an erbium:YAG (Er:YAG) laser (and also Nd-YAG, HF and CO lasers), to perform the above-mentioned laser surgery techniques. The infrared lasers emit light having a wavelength within the range of 0.8 micrometers (i.e., microns) to 5.5 microns which is essentially within the infrared light spectrum. Some infrared (e.g., Er:YAG) lasers are portable, solid state devices which typically cost between $50,000 and $100,000, which is much less expensive than excimer lasers. Furthermore, the infrared (e.g., Er:YAG) lasers typically are more durable and thus have a useful life span longer than that of the excimer type lasers. Also, the Er:YAG lasers use no toxic gas compared with the excimer lasers, and thus are much safer and easier to use.

As stated above, unlike excimer lasers which emit pulsed ultraviolet light (e.g., light having a wavelength of, for instance, 193 nm), the Er:YAG lasers emit light within the infrared range having a wavelength at or about 2.9 microns. Examples of laser surgery experiments performed with Er:YAG lasers are discussed in the following articles: Peyman et al. entitled "Long-Term Effect of Erbium-YAG Laser (2.9 μm) on the Primate Cornea", published in *International Ophthalmology*, Vol. 15, pp. 249–258 (1991); Peyman et al. entitled "Corneal Ablation in Rabbits Using an Infrared (2.9 μm) Erbium:YAG Laser", published in *Ophthalmology*, Vol. 96, No. 8, pp. 160–70 (August 1989); Seiler et al. entitled "Erbium: YAG Laser Photoablation of Human Cornea", published in *American Journal of Ophthalmology*, Vol. 120, No. 5, pp. 668–9 (November 1995), each of which is incorporated by reference herein in its entirety.

Although the infrared (e.g., Er:YAG) lasers are advantageous over the excimer lasers for the reasons discussed above, certain problems are experienced when infrared (e.g., Er:YAG) lasers are used to perform corneal modification. In particular, although the infrared radiation produced by an Er:YAG laser does ablate the surface of the live cornea to which it is directed, the ablation results in coagulation of the underlying corneal tissue to a depth of about 3–6 microns. This coagulation causes areas in the cornea to become soft and cloudy and thus, obstructs the vision of the eye. Although the coagulated tissue will eventually heal, the healing period is typically about three months, which is significantly longer than the healing period (e.g., about three days) for a cornea that was modified by similar techniques performed with an excimer laser.

Accordingly, a need exists for a system which can use an infrared and, in particular, an Er:YAG laser, to perform laser surgery on the eye to modify the cornea, but which does not experience the drawbacks associated with infrared laser (e.g., Er:YAG) eye surgery as known in the art.

SUMMARY OF THE INVENTION

An object of the present invention is to provide a system and method for using an infrared type (e.g., Er:YAG) laser to modify an external or internal surface of the cornea, while eliminating the coagulated tissue formed during the corneal ablation and thus reduce healing time.

A further object of the invention is to provide a system and method for effectively removing the coagulated tissue of an exterior or interior surface of a live cornea that was generated due to ablation by a laser.

These and other objects of the invention are substantially achieved by providing a system which employs an infrared type laser, such as an Er:YAG laser or the like, to ablate an exterior or interior surface of a live cornea to thus reshape or modify the live cornea and thereby change the refractive power of the cornea to correct ametropic conditions in the eye. The system further includes a device having a component which is placed in contact with the irradiated exterior or interior surface of the live cornea, and then manipulated to remove coagulated corneal tissue that was created by the irradiation of the laser light. The component can be any type of brush, metal device, diamond impregnated device, sponge, rubber, natural or artificial hair brush, or the like, that is rotated, vibrated or oscillated when in contact with the surface of the cornea to physically remove (e.g., erode) the coagulated portion of the cornea without removing any or essentially any other portion of the live cornea. The component also can be a fluid, such as a saline solution, that is directed toward the surface of the cornea that has been ablated by the laser beam to physically remove the coagulated portion of the surface. An irrigation and aspiration device can also be used in conjunction with the tool to aid in the physical removal of the coagulated portion of the live cornea. This irrigation and aspiration device can be integral with the tool, or a separate device that is used in conjunction with the tool.

DETAILED DESCRIPTION OF THE PREFERRED EMBODIMENTS

Figure 1:
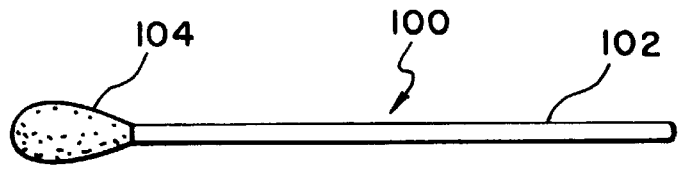
FIG. 1 illustrates an example of a tool for use in the system for modifying a live cornea by laser ablation and subsequent mechanical erosion according to an embodiment of the present invention.

FIG. 1 illustrates a side view of a tool 100 according to an embodiment of the present invention. As illustrated, the tool 100 includes a shaft 102 and a tip 104. The shaft can be made out of any suitable material such as plastic, metal, hard paper, wood, or the like. The tip 104 has an outer surface capable of physically removing, for example, eroding (i.e., physically removing through the use of a solid, liquid or gas) coagulated corneal tissue, and is somewhat rough or abusive relative to that tissue. The tip 104 is made of a material such as metal, diamond impregnated metal, sponge, rubber, a synthetic hair (e.g., nylon), wire hair or natural hair brush having bristles extending either radially or transverse to the shaft 102 or longitudinally in the direction of the shaft 102, cotton, or any suitable material that can be used to remove a coagulated portion of the live cornea as will be described below. The tip 104 can have any practical size or shape, and can have a diameter, for example, of 0.02 mm to 10 mm. In particular, if the tip 104 is a brush, it can have a diameter of 0.02 mm to 10 mm and be flat, cone shaped, or any suitable shape which is effective in removing coagulated corneal tissue. Also the brush can be dipped in a liquid (e.g., water) and frozen, and the frozen tip can be used to remove the coagulated portion of the live cornea. The tip 104 can be removable from shaft 102 so that different tips 104 can be used with the same shaft 102.

Figure 2:
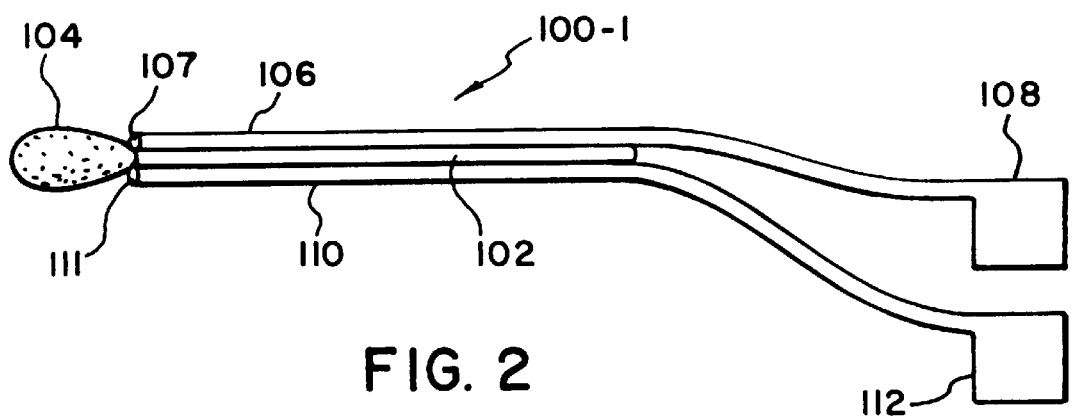
FIG. 2 is another example of a tool according to another embodiment the invention, which is used in the system of the present invention and which includes an irrigation and aspiration device.

Another embodiment of a tool 100-1 is shown in FIG. 2. Like tool 100, the tool 100-1 includes shaft 102 and tip 104 of the types described above. Furthermore, the tool 100-1 includes an irrigation conduit 106 that is capable of delivering a fluid such as water, saline solution, or any suitable fluid through an opening 107 in the conduit toward the tip 104. The conduit 106 is attached to a fluid providing device 108, such as a fluid pump, drip bottle, or the like, that contains the fluid to be delivered through the conduit 106 to the tip 104.

The tool 100-1 further includes a second conduit 110 that is used to aspirate or remove the fluid provided to the tip by conduit 106 as well as the coagulated tissue. That is, the conduit 110 is attached to a vacuum creating apparatus 112, such as a pump or any type of suction mechanism which creates a vacuum (e.g., 20–40 mm Hg) inside conduit 110 to draw at least a portion of the fluid delivered through conduit 106 and the coagulated tissue away from the tip 104 through opening 111, and through conduit 110. The conduits 106 and 110 can be made of any suitable material, such as plastic, rubber, or the like. Also, the conduits 106 and 110 can both be attached to or integral with the tool 100-1 as shown, or either or both of the conduits 106 and 110 can be physically separate from the tool 100-1.

Figure 3:
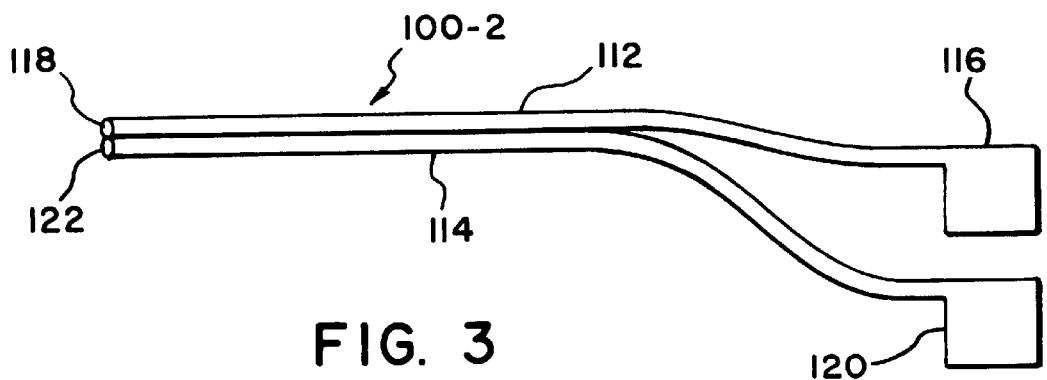
FIG. 3 is another example of a tool according to an embodiment of the present invention that is used in the system of the present invention, in which a fluid is used to erode or physically remove the coagulated portion of the live cornea.

Another example of a tool according to an embodiment of the present invention is shown in FIG. 3. As illustrated, the tool 100-2 includes conduits 112 and 114. Conduit 112 is attached to a fluid delivering device 116 that is operated to deliver under pressure a fluid, such as water, saline solution, air, a gas mixture or the like, through conduit 112, and out of the conduit opening 118. The fluid delivering device 116 delivers the fluid at such a pressure to be sufficient to physically remove (e.g., erode) a coagulated portion of a live cornea that was generated by irradiation of the live cornea with a laser beam.

As further illustrated, conduit 114 is attached to a vacuum creating device 120, such as a pump or any other type of suction device or the like which is capable of creating a vacuum in conduit 114. Accordingly, during operation, at least a portion of the fluid that is delivered through conduit 112 and out opening 118 is received into opening 122 in conduit 114 and thus drawn away from the opening 122 together with the coagulated tissue.

Figure 4:
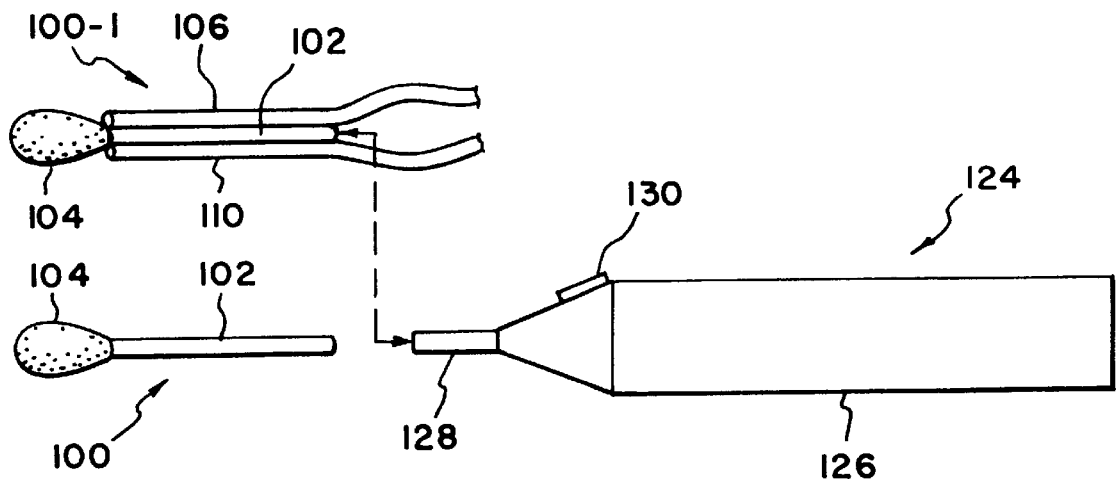
FIG. 4 is a side view of an example of a tool manipulating device for use with the examples of the tools shown in FIGS. 1 and 2.

FIG. 4 illustrates an example of a tool manipulating device 124 according to an embodiment of the present invention. As indicated, the tool manipulating device 124 includes a tool moving portion 126 and a driving device 128 that is powered by a battery, electrical outlet (not shown), spring-wound mechanism, pneumatic air pressure system or any other suitable driving device that can deliver a driving motion to the moving portion 126.

Specifically, as illustrated, the shaft 102 of tool 100 (or tool 100-1) is removably attachable to the tool moving portion 126. Accordingly, when an on-off switch 130 of the tool manipulating device is placed in the "on" position, the tool moving portion 126 moves under the power of the driving device 128 and thus, moves the tool 100 (or tool 100-1) in a corresponding manner. The tool moving portion 126 is configured to oscillate, rotate or vibrate under the driving force provided by the driving device 128 and thus, oscillates, rotates or vibrates the tool 100 (or tool 100-1) at any suitable speed sufficient to remove coagulated corneal tissue. For example, the tool moving portion 126 can rotate the tool 100 or 100-1 at speeds of 1 rev/minute to, e.g., 5000 rev/minute or more, as desired. A specific example can be 200–300 rev/minute.

Examples of the applications in which tools 100, 100-1 and 100-2 described above can be used will now be described.

Figure 5:
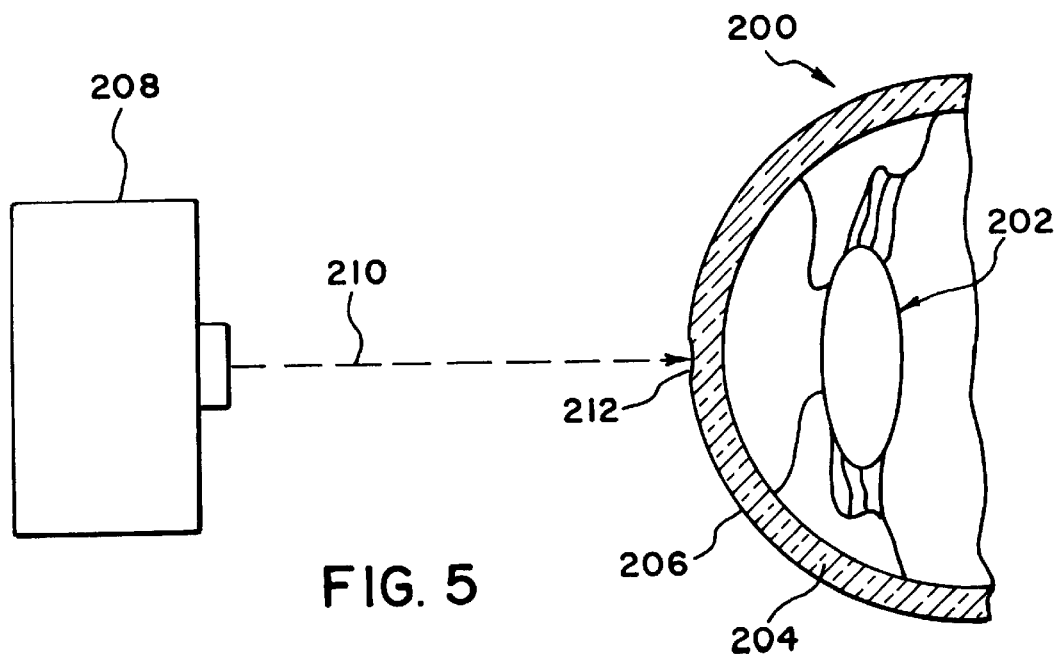
FIG. 5 is a cross-sectional view of an eye whose outer corneal surface is being ablated by a laser.

FIG. 5 is a cross-sectional view of an eye 200 that is undergoing laser surgery. As shown, the eye includes a lens 202 and a cornea having an outer surface 206.

A laser 208, which is preferably an infrared laser such as an Er:YAG laser of the type described above, is used to generate infrared laser light having a wavelength within the infrared light spectrum. The wavelength of the laser light 210 delivered by an Er:YAG laser is at or about 2.9 micrometers, i.e., 2.9 microns.

Figure 6:
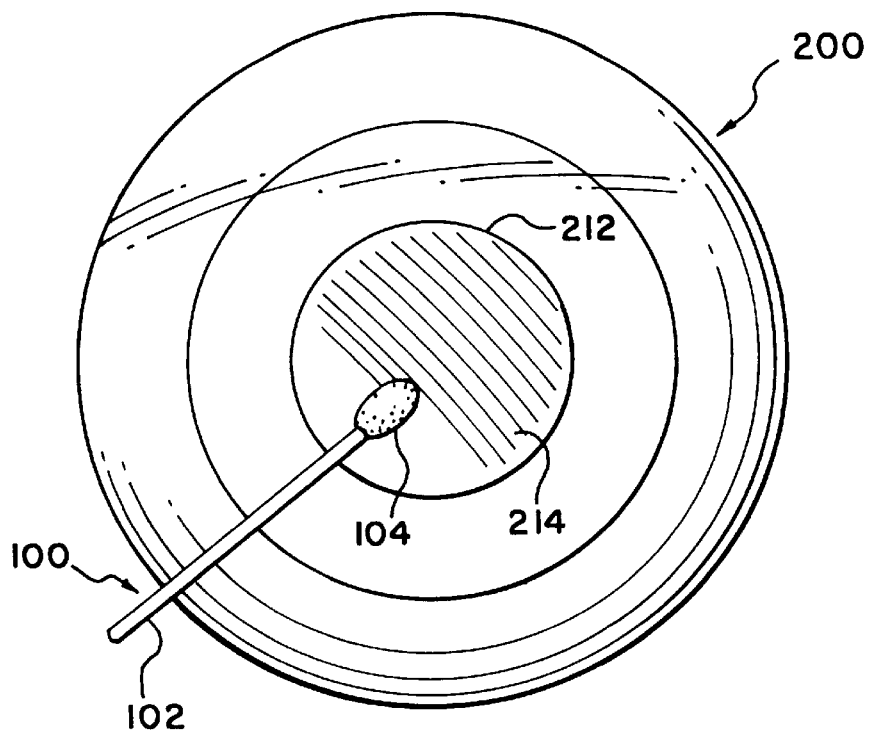
FIG. 6 is a front view of the eye shown in FIG. 5 that has been ablated by the laser such that a coagulated portion has been formed, and an example of the tool according to the present invention that is being used to remove the coagulated portion.

Other types of infrared lasers, such as Nd-YAG, HF and CO can also be used. The infrared lasers emit light having a wavelength within a range of about 0.8 microns to about 5.5 microns. The laser light 210 is directed toward the outer surface 206 of the cornea 204 to photoablate a target area 212 of the outer surface 206. Specifically, as shown in FIG. 6, which is a front elevational view of the eye 200 shown in FIG. 5, the target area 212 becomes photoablated by the laser light 210. However, as discussed above, the infrared laser light creates a coagulated area 214 of the cornea 204 underneath the target area 212. Typically, this coagulated area 214 is about 3 microns–6 microns deep into the cornea 204.

As discussed above, this coagulated portion 214 takes a significantly long time (e.g., up to three months) to heal. Accordingly, as further shown in FIG. 6, the tool 100 (or 100-1 or 100-2) is used to physically remove the coagulated portion 214 of the cornea that was created due to the irradiation of the surface 206 of the cornea by the laser light 210. Specifically, the manipulating member 124 is configured to enable an operator to place the tip 104 in contact with the coagulated area 214. The driving member 126 then oscillates, rotates or vibrates the tool 100 (or 100-1) when the tip 104 is in contact with the coagulated area 214, so that the material of which the tip 104 is made begins to physically remove (e.g., erode), the coagulated tissue 214 from the remainder of the cornea 204.

Figure 7:
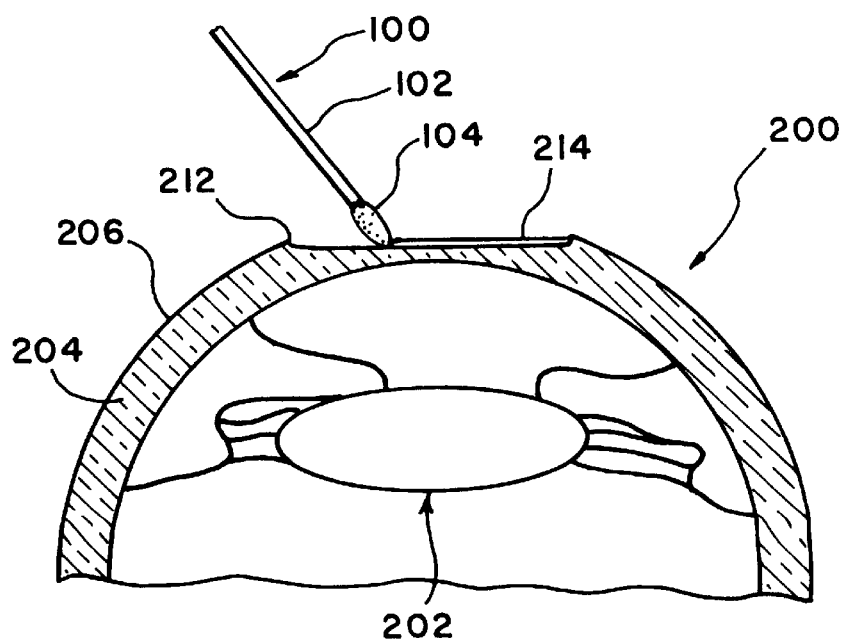
FIG. 7 is a side view of the eye as shown in FIG. 6 in which the tool is being used to remove the coagulated portion of the live cornea.

This phenomenon is better illustrated in FIG. 7. As indicated, the tip 104 of the tool 100 (or 100-1) is manipulated so as to remove the coagulated portion 214 of the cornea without removing any or essentially any of the remaining portion of the cornea 204. The manipulating tool 124 can be controlled by an operator to cause the tip 104 of the tool 100 (or 100-1) to apply the appropriate amount of pressure to the coagulated area 214 so as to remove only or essentially only the coagulated area 214.

As stated, the tool 100 (or 100-1) can be used with the manipulating member 124 to remove the coagulated area 214. Alternatively, an operator can use the tool 100 or 100-1 by itself to remove the coagulated area 214.

Furthermore, the tool 100-2 (FIG. 3) can be used to remove the coagulated tissue 214. Specifically, the open ends 118 and 122 are placed in contact with or proximate to the coagulated area 214, so that as the fluid delivered through conduit 112 is ejected out of the opening 118, the fluid contacts and thus physically removes the coagulated area 214. At least a portion of the fluid, as well as the coagulated tissue, can then be removed from the coagulated area 214 by being drawn into opening 122 and through conduit 114 by the vacuum created by vacuum creating device 120.

Additionally, it is noted that any of tools 100, 100-1 and 100-2 can be used in the manner described above to instead remove most of the coagulated area 214, as opposed to all or substantially all of the coagulated area 214. For instance, the tools 100, 100-1 or 100-2 can be used to remove all but about 1 micron of the coagulated area 214. Another tool 100 or 100-1 having a tip 104 made of a material having a texture which is, for instance, different from and preferably somewhat smoother or less abrasive than that of the tip 104 of the initial tool 100, 100-1 or 100-2 can then be used in a manner similar to the initial tool 100, 100-1 or 100-2 to remove the remaining portion (e.g., 1 or about 1 micron or less) of the coagulated area 214 to expose the underlying corneal tissue. That second tool 100 or 100-1 can then be used to polish that underlying corneal tissue. Tool 100-2 can also be used as the second tool that removes the remaining portion of the coagulated area and which polishes the underlying cornea.

Figure 8:
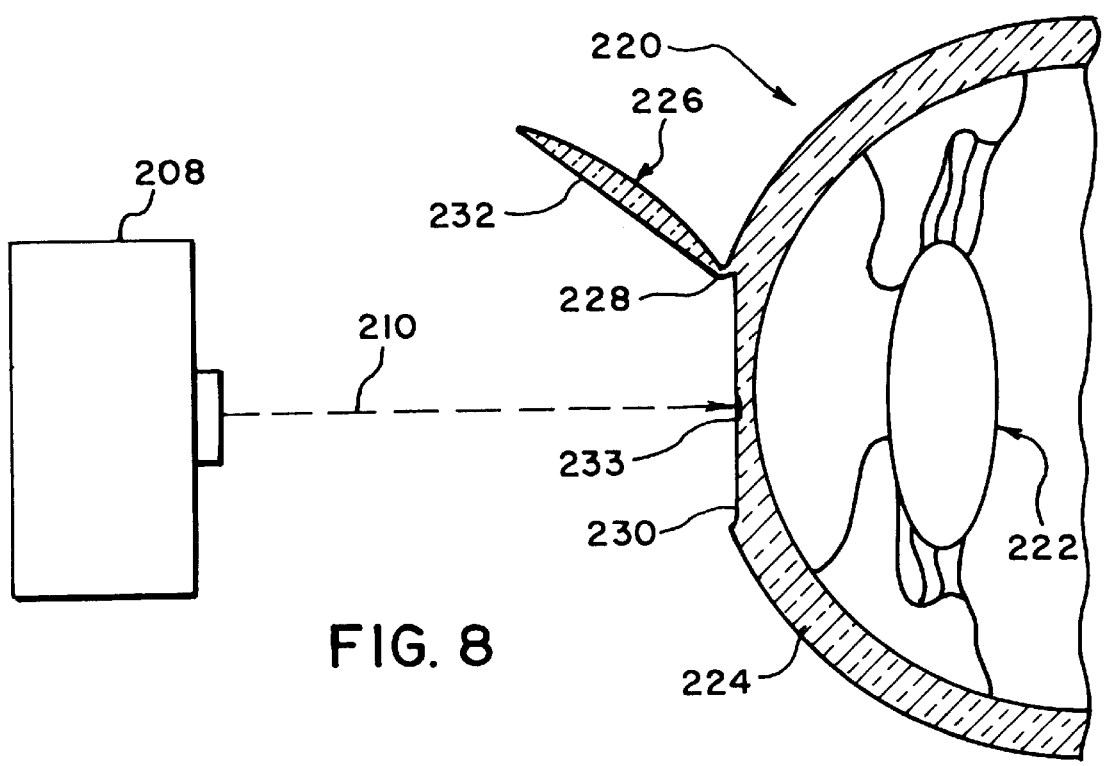
FIG. 8 is a cross-sectional view of an eye having a flap-like surface removed to expose an inner surface of the live cornea of the eye, which is being ablated by a laser beam.

As discussed above, the tools 100, 100-1 and 100-2 can be used to remove coagulated areas of the cornea that are formed on an interior surface of the cornea when a LASIK process is performed to modify or change the shape of the cornea. Specifically, FIG. 8 shows a cross-sectional view of an eye 220 including a lens 222 and cornea 224. As described in U.S. Pat. No. 4,840,175 to Peyman, a flap-like layer 226 of the cornea 224 is formed by separating the flap-like layer 226 from the cornea 224 with a cutting tool, such as a microkeratome, excimer (e.g., ultraviolet) laser, infrared (e.g., Er:YAG) laser, or the like. The flap-like layer 226 can remain attached to the cornea 224 by an attaching portion 228. When the flap-like layer 226 is folded back or pivoted about the attaching portion 228, an inner surface 230 of the cornea 224 is exposed. Also, an inner surface 232 of the flap-like layer 226 is exposed.

As illustrated in FIG. 8, a laser 208, which is, for example, an infrared laser (e.g., an Er:YAG laser) is used to ablate the inner surface 230 of the cornea 224. Specifically, the infrared light 210 is directed onto a target area 233 of the exposed surface 230, and thus ablates the target area 233.

Figure 9:
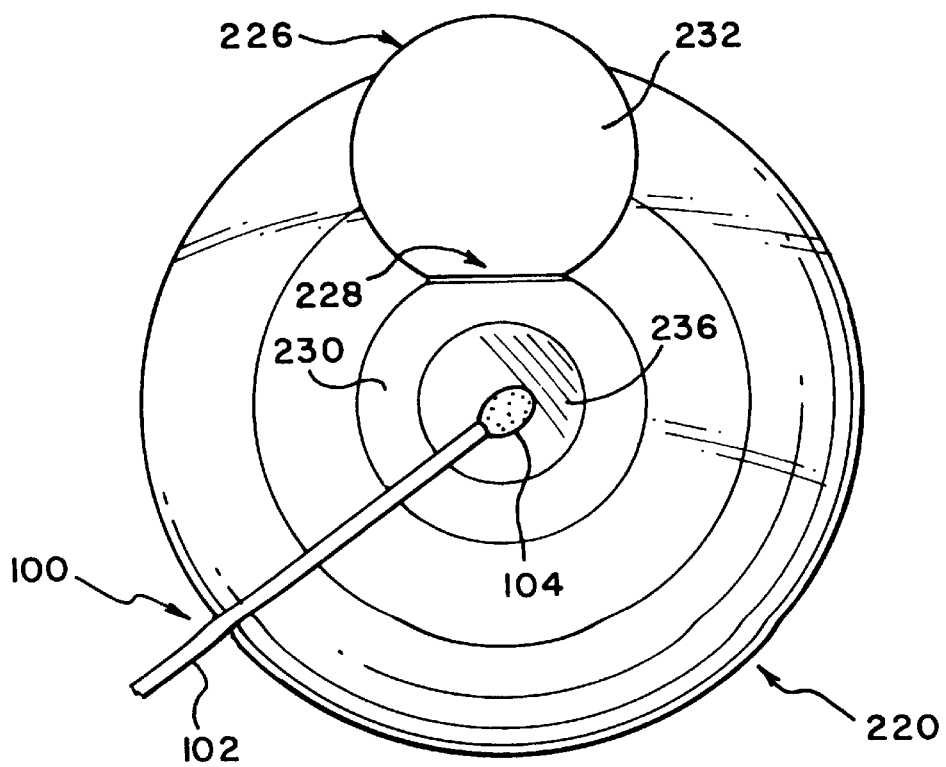
FIG. 9 is a front view showing the coagulated portion of the eye shown in FIG. 8 that was created by the irradiation of the laser light, and which is being removed by the tool according to the embodiments of the present invention.
Figure 10:
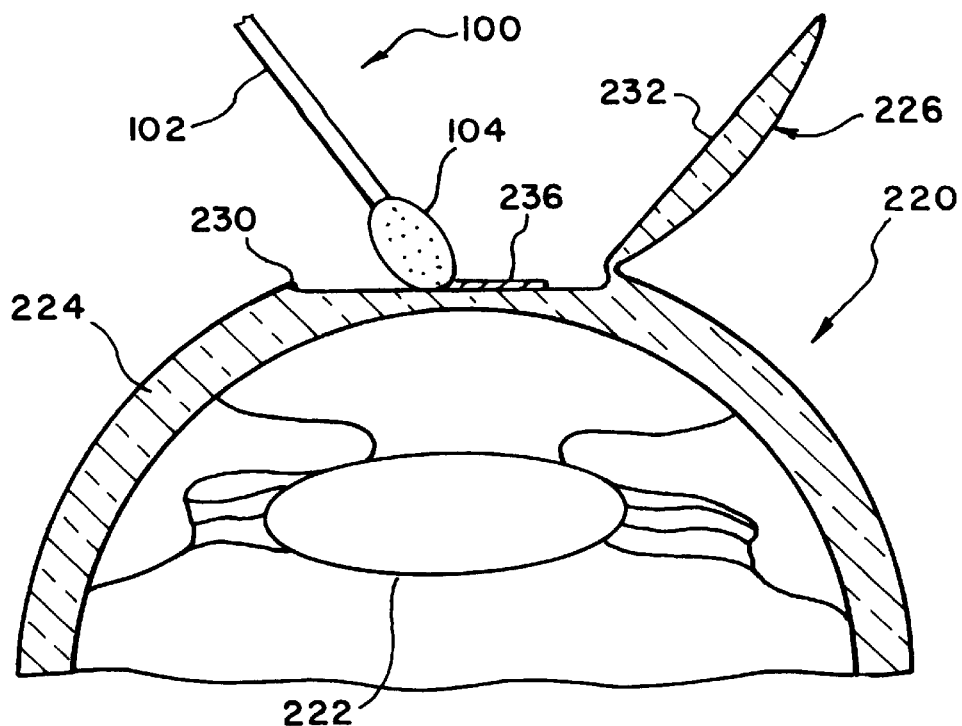
FIG. 10 is an enlarged side view of the eye as shown in FIG. 9 in which the coagulated portion is being removed.

However, as described above, the infrared Er:YAG laser creates a coagulated portion of the cornea 224 that is about 3 microns–6 microns deep at the target area 232 as shown, for example, in FIG. 9. Accordingly, as further shown in FIG. 9, the tool 100 (or 100-1 or 100-2) can be used to remove the coagulated portion 236 from the cornea 224 without removing any or essentially any of the cornea 224.

That is, as described above, the tool 100 (or 100-1) can be attached to the manipulating member 124, which positions the tip 104 of the tool 100 (or 100-1) to contact the coagulated area 236. The manipulating member 124 oscillates, rotates or vibrates the tool 100 (or 100-1) to cause the material of the tip 104 to erode or physically remove the coagulated area 236. The manipulating tool 124 enables an operator to apply the appropriate amount of pressure to the coagulated area 236 by tip 104 to remove the coagulated area 236 without removing any or substantially any of the remaining portion of the cornea 224.

Also, if the flap-like layer 226 was separated from the cornea 224 through the use of a laser and, in particular, an infrared (Er:YAG) laser, the tool 100 (or 100-1 or 100-2) can be used to remove any and all coagulated cornea tissue present on the inner surface 232 of the flap-like layer 226 in a similar manner. It is noted that if the tool 100-2 is used to remove the coagulated portion at either the inner surface 230 of the cornea 224 or the inner surface 232 of the flap-like layer 226, the opening 118 is positioned so that the fluid that passes through conduit 112 contacts the coagulated area physically removes (e.g., erodes) the coagulated area without removing any or essentially any of the underlying corneal tissue that has not been coagulated.

Additionally, it is noted that any of tools 100, 100-1 and 100-2 can be used in the manner described above to instead remove most of the coagulated area 236, as opposed to all or substantially all of the coagulated area 236. That is, the tool 100, 100-1 or 100-2 can be used to remove all but 1 or about 1 micron of the coagulated area 236. Another tool 100 or 100-1 having a tip 104 made of a material having a texture which is, for instance, different from and preferably somewhat smoother or less abrasive than that of the tip 104 of the initial tool 100, 100-1 or 100-2 can then be used in a manner similar to the initial tool 100, 100-1 or 100-2 to remove the remaining portion (e.g., 1 or about 1 micron or less) of the coagulated area 236 to expose the underlying corneal tissue. That second tool 100 or 100-1 can then be used to polish that underlying corneal tissue. Tool 102-1 can also be used as the second tool that removes the remaining portion of the coagulated area and which polishes the underlying cornea.

After the tools 100, 100-1 and 100-2 have been used in the manner described above to remove the coagulated area on the surface 230 and the inner surface 232 of the flap-like layer 226, and, if desired, to polish the underlying corneal tissue of the surfaces 230 and 232, the flap-like layer 226 can then be reattached over the inner surface 230 from which the coagulated area 236 has been removed, so that the reattached flap-like layer 226 assumes a shape conforming to that of the modified inner surfaces.

Figure 11:
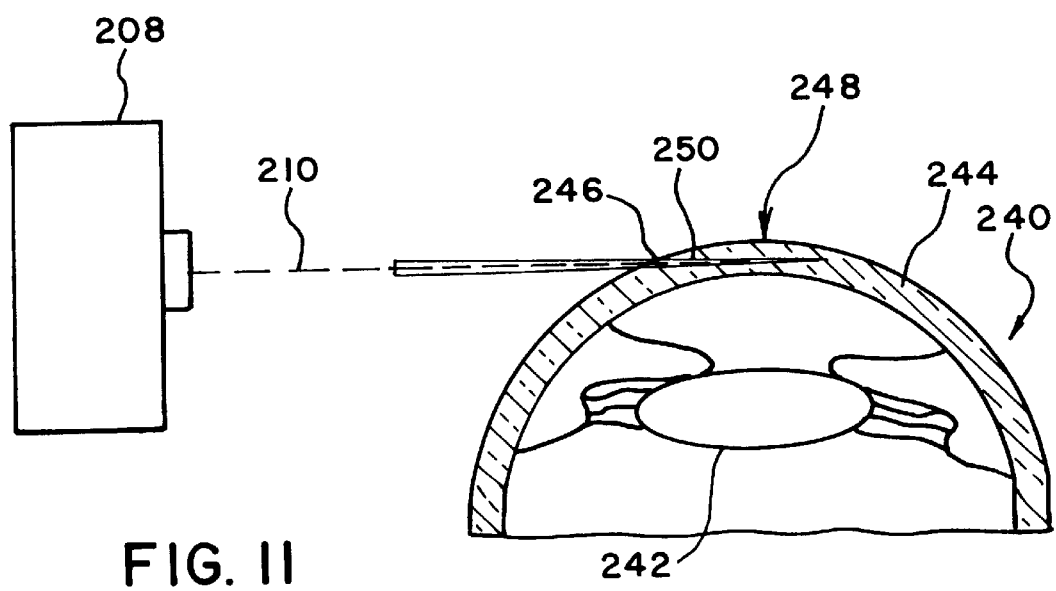
FIG. 11 is a cross-sectional view of an eye having a cornea into which a pocket is being formed and the internal surfaces are irradiated by a laser.
Figure 12:
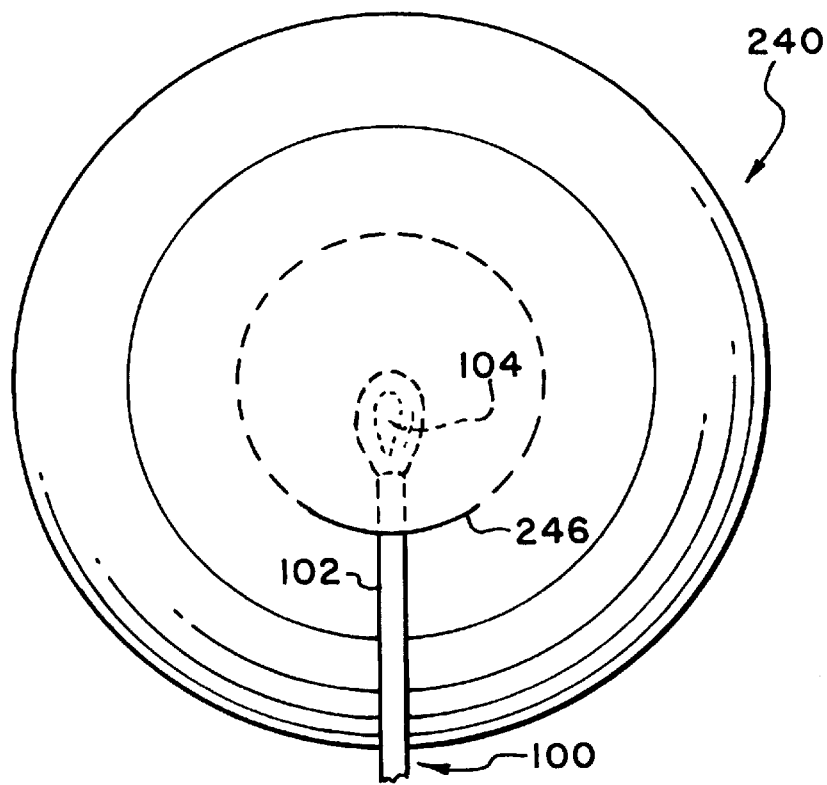
FIG. 12 is a front view of the eye shown in FIG. 11 having a pocket that was formed in the cornea by the laser with a tool located in the pocket.

The tools 100, 100-1 and 100-2 can also be used to remove coagulated areas of the cornea that develop if an infrared (Er:YAG) laser is used to create a pocket in the cornea. Specifically, FIGS. 11 and 12 show a cross-section of an eye 240 having a lens 242 and a cornea 244. An infrared Er:YAG laser can be used after an internal keratome device has created a pocket 246 between an outer layer 248 of the cornea and the remainder of the cornea 244.

In creating the pocket 246, the laser 208 directs the infrared light 210 via a fiber optic 211 toward the cornea 244 at the desired location. The focal point of the laser light 210 can be moved as necessary to ablate the desired portions of the cornea 244 in the pocket 246 between the outer layer 248 of the cornea and the remaining portion of the cornea 244.

However, when the cornea is being ablated, coagulated portions 250 are formed at a depth of 3 microns–6 microns from the pocket 246 in both the remaining portion of the cornea 244 and the outer layer 248 of the cornea.

Figure 13:
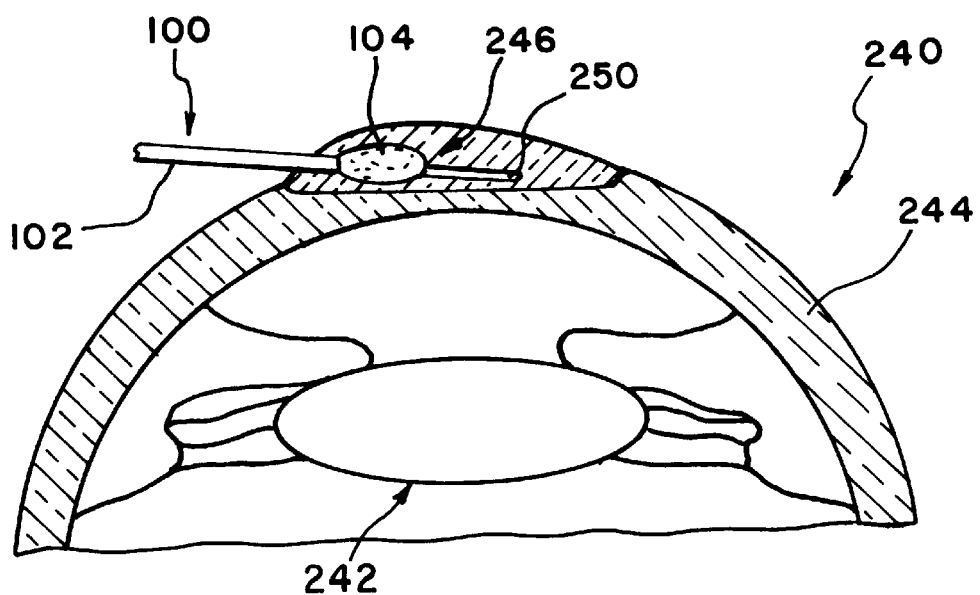
FIG. 13 is a cross-sectional side view of the eye shown in FIG. 12 in which a tool according to the embodiments of the present invention is being used to remove the coagulated portion of the cornea.

As shown in FIGS. 12 and 13, the tip 104 of tool 100 (or 100-1) can be inserted into the pocket 246 to physically remove (e.g., erode) the coagulated portion 250 of the corneal tissue. In a manner similar to that described above, the tool 100 (or 100-1) can be attached to the manipulating member 124, and oscillated, rotated or vibrated by the manipulating member 124 to physically remove the coagulated area 250.

The tool 100-2 can also be used to remove the coagulated area 250. In this event, the tip of the tool 100-2 having openings 118 and 122 is inserted into the pocket 246. The fluid that travels through conduit 112 and out of opening 118 physically removes the coagulated portion 250 without removing any or essentially any of the underlying cornea in the remaining portion of the cornea 244 or outer layer of cornea 248. Some of the fluid can enter opening 122 and be removed along with the coagulated tissue through conduit 114 by the vacuum created by vacuum creating device 120.

Additionally, it is noted that any of tools 100, 100-1 and 100-2 can be used in the manner described above to instead remove most of the coagulated area 250, as opposed to all or substantially all of the coagulated area 250. For instance, the tools 100, 100-1 or 100-2 can be used to remove all but 1 micron or about 1 micron of coagulated area 250. Another tool 100 or 100-1 having a tip 104 made of a material having a texture which is, for instance, different from and preferably somewhat smoother or less abrasive than that of the tip 104 of the initial tool 100, 100-1 or 100-2 can them be used in a manner similar to the initial tool 100, 100-1 or 100-2 to remove the remaining portion (e.g., 1 or about 1 micron or less) of the coagulated area 250 to expose the underlying corneal tissue. That second tool 100 or 100-1 can them be used to polish that underlying corneal tissue. Tool 100-2 can also be used as the second tool that removes the remaining portion of the coagulated area and which polishes the underlying cornea.

Furthermore, if the pocket 246 has been expanded into a flap-like layer as shown, for example, in FIGS. 8–9, the tools 100, 100-1 and 100-2 can also be used in the manner described above to remove the coagulated area 250 on the inner surface of the flap-like layer and inner surface of the cornea, and, if desired, to polish the underlying cornea tissue of those inner surfaces. The flap-like layer can then be reattached over the inner surface of the cornea from which the coagulated area has been removed, so that the reattached flap-like layer assumes a shape conforming to that of the modified inner surfaces.

By using the tools 100, 100-1 or 100-2, or any variations thereof, the coagulated portion of the cornea that is created due to irradiation of the cornea by laser light from an ER:YAG laser can be removed, thus decreasing the amount of healing time needed and improving the overall quality of the patient's vision.

Figure 14A:
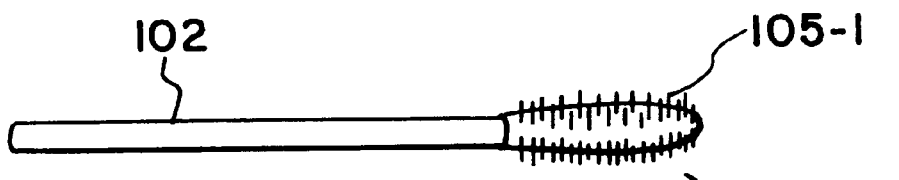
FIGS. 14A–14D illustrate examples of different types of brushes that can be used as the tip of the tools shown in FIGS. 1 and 2.
Figure 14B:
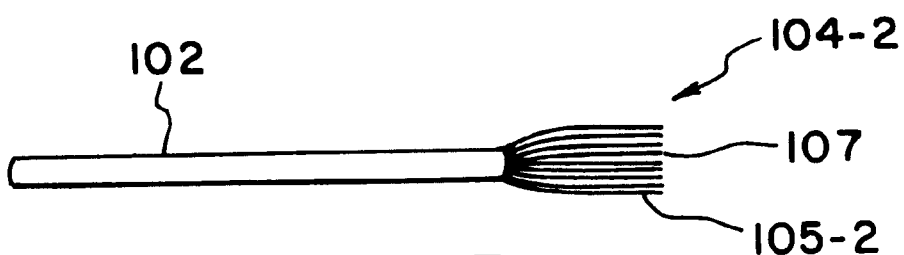
Figure 14C:
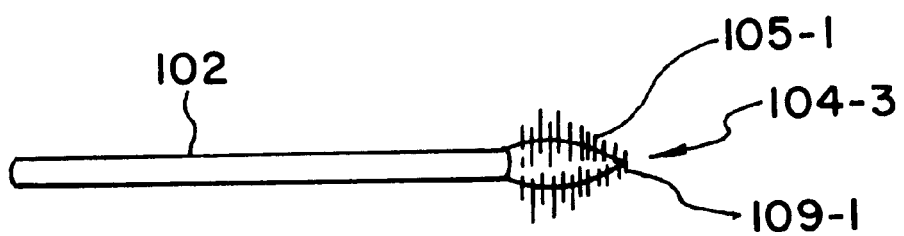
Figure 14D:
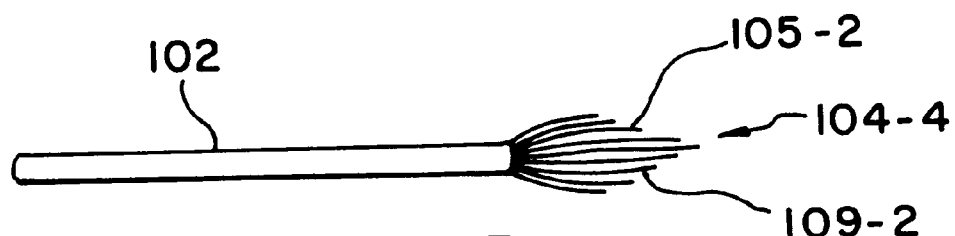

As discussed above, the tip 104 of the tools 100 and 100-1 can be made of any suitable material and have any suitable shape. For example, as shown in FIG. 14A, the tip 104 can be a brush 104-1 having natural or artificial hair bristles 105-1 extending transversely or radially to the shaft 102. As shown in FIG. 14B, the tip 104 can be a brush 104-2 having natural or artificial hair bristles 105-2 extending in a direction longitudinally of the shaft 102. As further shown, the bristles 105-2 form a flat or relatively flat end 107 of the brush 104-2. Alternatively, as shown in FIGS. 14C and 14D, the bristles 105-1 and 105-2 can be arranged such that the brushes 104-3 and 104-4 have cone shaped tips 109-1 and 109-2.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims.

What is claimed is:

1. A system, adaptable for reshaping an area of corneal tissue of a live cornea, comprising:

a laser, adapted to irradiate an inner or outer surface of the live cornea to ablate the irradiated surface and create a coagulated area of corneal tissue;

a component which is adapted to contact the coagulated area of corneal tissue to physically remove at least a portion of the coagulated area from the live cornea, the component comprising one of the following: a metal, sponge, brush, fabric, rubber element or diamond containing material; and a device which is configured to place the component in contact with the coagulated area to enable the component to physically remove the portion of the coagulated area.

2. A system as claimed in claim 1, wherein the component is a fluid; and the device comprising a fluid delivery system which directs the fluid toward the coagulated area so that the fluid erodes the portion of the coagulated area.

3. A system as claimed in claim 2, further comprising:

a suction device which removes at least a portion of the fluid from the coagulated area.

4. A system as claimed in claim 1, wherein the component removes substantially all of the coagulated area.

5. A system as claimed in claim 1, wherein the device is configured to enable the component to remove the portion of the coagulated area from the live cornea without removing substantially any other corneal tissue from the live cornea.

6. A system as claimed in claim 1, wherein the laser is an infrared laser.

7. A system as claimed in claim 6, wherein the infrared laser emits light having a wavelength in the range of 0.8 microns to 5.5 microns.

8. A system as claimed in claim 7, wherein the light has a wavelength of about 2.9 microns.

9. A system as claimed in claim 1, wherein the laser is an Erbium:YAG laser.

10. A system as claimed in claim 1, further comprising:

a fluid delivery system which directs a fluid toward the coagulated area when the component is removing the portion of the coagulated area.

11. A system as claimed in claim 10, further comprising:

a suction device which removes at least a portion of the fluid from the coagulated area.

12. As system, adaptable for reshaping an area of corneal tissue of a live cornea, comprising:

a laser, adapted to irradiate an inner or outer surface of the live cornea to ablate the irradiated surface and create a coagulated area of corneal tissue;

a component which is adapted to contact the coagulated area of corneal tissue to physically remove at least a portion of the coagulated area from the live cornea; and a device which is configured to place the component in contact with the coagulated area to enable the component to physically remove the portion of the coagulated area, the device comprising a movable member which is configured to move the component when the component contacts the coagulated area.

13. A system as claimed in claim 12, wherein the movable member is one of the following:

a vibrator which is configured to vibrate the component when the component contacts the coagulated area; and a rotator which is configured to rotate the component when the component contacts the coagulated area.

14. A system, adaptable for reshaping an area of corneal tissue of a live cornea, comprising:

a laser, adapted to irradiate an inner or outer surface of the live cornea to ablate the irradiated surface and create a coagulated area of corneal tissue;

a component which is adapted to contact the coagulated area of corneal tissue to physically remove at least a portion of the coagulated area from the live cornea;

a device which is configured to place the component in contact with the coagulated area to enable the component to physically remove the portion of the coagulated area;

a second component which is adaptable to contact a remaining portion of the coagulated area of corneal tissue which remains after the component has removed the portion of the coagulated area, to physically remove at least a portion of the remaining portion of the coagulated area from the live cornea; and the device being further configured to place the second component in contact with the remaining portion of the coagulated area to physically remove the remaining portion.

15. A system as claimed in 14, wherein the device comprises a coupling portion, configured to selectably couple to the component and second component, such that the component is coupled to the coupling portion when the device is configured to place the component in contact with the portion of the coagulated area, and the second component is coupled to the coupling portion when the device is configured to place the second component in contact with the remaining portion of the coagulated area.

16. A system as claimed in claim 14, wherein the second component has a texture different from that of the component.

17. A system as claimed in claim 14, wherein the second component is one of the following metal, sponge, brush, fabric, rubber or diamond containing material.

* * * * *